(12) United States Patent
Overes et al.

(10) Patent No.: US 8,915,964 B2
(45) Date of Patent: Dec. 23, 2014

(54) FLEXIBLE DAMPENING INTERVERTEBRAL SPACER DEVICE

(75) Inventors: Thomas Overes, Langendorf (CH); Beat Lechmann, Grenchen (CH); Silas Zurschmiede, Grenchen (CH); Cyril Voisard, Niederbipp (CH); Urs Hulliger, Deitlingen (CH); Robert Frigg, Bettlach (CH)

(73) Assignee: DePuy Synthes Products, LLC, Raynham, MA (US)

( * ) Notice: Subject to any disclaimer, the term of this patent is extended or adjusted under 35 U.S.C. 154(b) by 175 days.

(21) Appl. No.: 13/002,867

(22) PCT Filed: Jul. 14, 2009

(86) PCT No.: PCT/US2009/050597
§ 371 (c)(1),
(2), (4) Date: Jan. 6, 2011

(87) PCT Pub. No.: WO2010/009168
PCT Pub. Date: Jan. 21, 2010

(65) Prior Publication Data
US 2011/0118845 A1    May 19, 2011

Related U.S. Application Data

(60) Provisional application No. 61/080,497, filed on Jul. 14, 2008.

(51) Int. Cl.
*A61F 2/44* (2006.01)
*A61F 2/32* (2006.01)
(Continued)

(52) U.S. Cl.
CPC .............. *A61F 2/4425* (2013.01); *A61F 2/32* (2013.01); *A61F 2/38* (2013.01);
(Continued)

(58) Field of Classification Search
USPC ........................................... 623/17.11–17.16
See application file for complete search history.

(56) References Cited

U.S. PATENT DOCUMENTS 6,315,797 B1 * 11/2001 Middleton ................. 623/17.16
6,517,580 B1    2/2003 Ramadan et al.
(Continued)

FOREIGN PATENT DOCUMENTS

| EP | 0 677 277 | 10/1995 |
|---|---|---|
| EP | 2042128 | 4/2009 |

(Continued)

OTHER PUBLICATIONS

International Patent Application No. PCT/US2009/050597: International Search Report and Written Opinion dated Oct. 29, 2009, 15 pages.

*Primary Examiner* — Mary Hoffman
*Assistant Examiner* — Michelle C Eckman
(74) *Attorney, Agent, or Firm* — Baker & Hostetler LLP

(57) ABSTRACT

A flexible dampening intervertebral spacer (100) to replace a spinal disc comprising upper and lower plates (101,103), an articulation element (102) and optional intermediate members (804,805). The articulation element has a plurality of interposed, concentric ring shaped segments (202) separated by one or more spaces (201) and one or more bridging elements (203) connecting the interposed segments. A first portion of the articulation element, preferably an innermost segment, is preferably fixedly connected to the upper plate while a second portion of the articulation element, preferably the outermost segment, is preferably connected to the lower plate to permit relative movement of the endplates by elastic deflection or flexing of the articulation element without opposed surfaces rubbing against each other.

31 Claims, 10 Drawing Sheets

(51) Int. Cl.
  *A61F 2/38* (2006.01)
  *A61F 2/40* (2006.01)
  *A61F 2/42* (2006.01)
  *A61F 2/30* (2006.01)

(52) U.S. Cl.
  CPC ............... *A61F 2/40* (2013.01); *A61F 2/4202* (2013.01); *A61F 2/4225* (2013.01); *A61F 2/4241* (2013.01); *A61F 2/4261* (2013.01); *A61F 2/44* (2013.01); *A61F 2/442* (2013.01); *A61F 2002/30004* (2013.01); *A61F 2002/30133* (2013.01); *A61F 2002/30187* (2013.01); *A61F 2002/302* (2013.01); *A61F 2002/30324* (2013.01); *A61F 2002/30327* (2013.01); *A61F 2002/30332* (2013.01); *A61F 2002/30354* (2013.01); *A61F 2002/30383* (2013.01); *A61F 2002/30426* (2013.01); *A61F 2002/30454* (2013.01); *A61F 2002/30471* (2013.01); *A61F 2002/30481* (2013.01); *A61F 2002/305* (2013.01); *A61F 2002/30563* (2013.01); *A61F 2002/30594* (2013.01); *A61F 2002/30598* (2013.01); *A61F 2002/30604* (2013.01); *A61F 2002/30616* (2013.01); *A61F 2002/30733* (2013.01); *A61F 2002/30738* (2013.01); *A61F 2002/30841* (2013.01); *A61F 2002/30884* (2013.01); *A61F 2002/30892* (2013.01); *A61F 2002/30904* (2013.01); *A61F 2002/30919* (2013.01); *A61F 2002/30968* (2013.01); *A61F 2002/3097* (2013.01); *A61F 2002/443* (2013.01); *A61F 2220/0025* (2013.01); *A61F 2220/0033* (2013.01); *A61F 2220/0058* (2013.01); *A61F 2220/0091* (2013.01); *A61F 2230/0015* (2013.01); *A61F 2230/0034* (2013.01); *A61F 2230/0065* (2013.01); *A61F 2250/0014* (2013.01); *A61F 2250/0036* (2013.01); *A61F 2250/0039* (2013.01); *A61F 2310/00017* (2013.01); *A61F 2310/00023* (2013.01); *A61F 2310/00029* (2013.01); *A61F 2310/00179* (2013.01)
  USPC ...................................................... 623/17.16

(56) References Cited

U.S. PATENT DOCUMENTS

| | | | | |
|---|---|---|---|---|
| 6,579,321 | B1 * | 6/2003 | Gordon et al. | 623/17.16 |
| 6,682,562 | B2 * | 1/2004 | Viart et al. | 623/17.14 |
| 7,001,433 | B2 * | 2/2006 | Songer et al. | 623/17.16 |
| 7,087,082 | B2 * | 8/2006 | Paul et al. | 623/17.11 |
| 7,166,131 | B2 * | 1/2007 | Studer et al. | 623/17.16 |
| 7,291,171 | B2 * | 11/2007 | Ferree | 623/17.11 |
| 7,419,505 | B2 * | 9/2008 | Fleischmann et al. | 623/17.11 |
| 7,419,506 | B2 * | 9/2008 | Hestad et al. | 623/17.16 |
| 2002/0111685 | A1 * | 8/2002 | Ralph et al. | 623/17.13 |
| 2003/0014112 | A1 * | 1/2003 | Ralph et al. | 623/17.13 |
| 2004/0111155 | A1 * | 6/2004 | Ferree | 623/17.13 |
| 2004/0220570 | A1 | 11/2004 | Frigg | |
| 2005/0216084 | A1 * | 9/2005 | Fleischmann et al. | 623/17.11 |
| 2005/0234554 | A1 * | 10/2005 | Ralph et al. | 623/17.13 |
| 2005/0251260 | A1 * | 11/2005 | Gerber et al. | 623/17.13 |
| 2006/0052872 | A1 * | 3/2006 | Studer et al. | 623/17.13 |
| 2006/0229608 | A1 | 10/2006 | Foster et al. | |
| 2006/0276790 | A1 | 12/2006 | Dawson et al. | |
| 2006/0276900 | A1 * | 12/2006 | Carpenter | 623/17.15 |
| 2007/0016200 | A1 | 1/2007 | Jackson | |
| 2007/0067038 | A1 * | 3/2007 | Studer et al. | 623/17.13 |
| 2007/0123990 | A1 * | 5/2007 | Sharifi-Mehr | 623/17.16 |
| 2007/0179613 | A1 * | 8/2007 | Heinz | 623/17.12 |
| 2007/0270860 | A1 | 11/2007 | Jackson | |
| 2008/0033433 | A1 | 2/2008 | Implicito | |
| 2008/0097434 | A1 | 4/2008 | Moumene et al. | |
| 2008/0161919 | A1 * | 7/2008 | Melkent | 623/17.11 |
| 2008/0161924 | A1 | 7/2008 | Viker | |
| 2008/0167686 | A1 * | 7/2008 | Trieu et al. | 606/249 |
| 2009/0076614 | A1 * | 3/2009 | Arramon | 623/17.16 |
| 2009/0088850 | A1 * | 4/2009 | Froehlich | 623/17.16 |
| 2009/0093819 | A1 | 4/2009 | Joshi | |
| 2009/0118836 | A1 * | 5/2009 | Cordaro | 623/17.16 |
| 2009/0177283 | A9 * | 7/2009 | Ralph et al. | 623/17.15 |
| 2009/0192617 | A1 * | 7/2009 | Arramon et al. | 623/17.16 |
| 2009/0281629 | A1 * | 11/2009 | Roebling et al. | 623/17.16 |

FOREIGN PATENT DOCUMENTS

| | | |
|---|---|---|
| FR | 2734148 | 11/1996 |
| WO | WO 00/23014 | 4/2000 |
| WO | WO 01/56489 | 8/2001 |
| WO | WO 2006/066053 | 6/2006 |
| WO | WO 2007/103404 | 9/2007 |
| WO | WO 2010/009168 | 1/2010 |

* cited by examiner

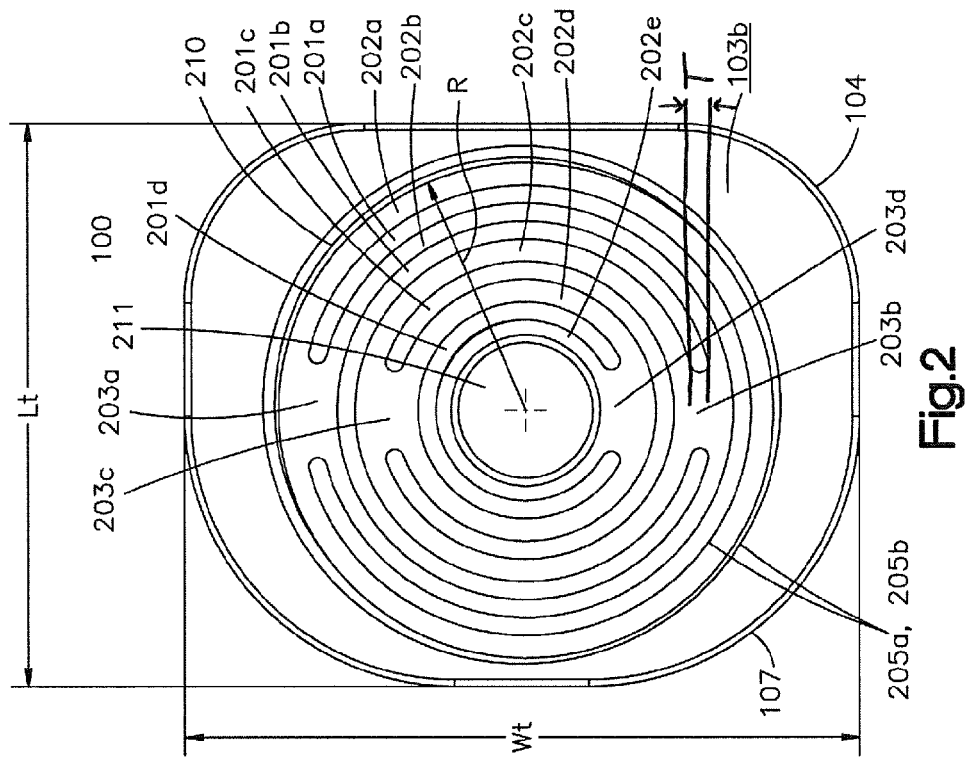
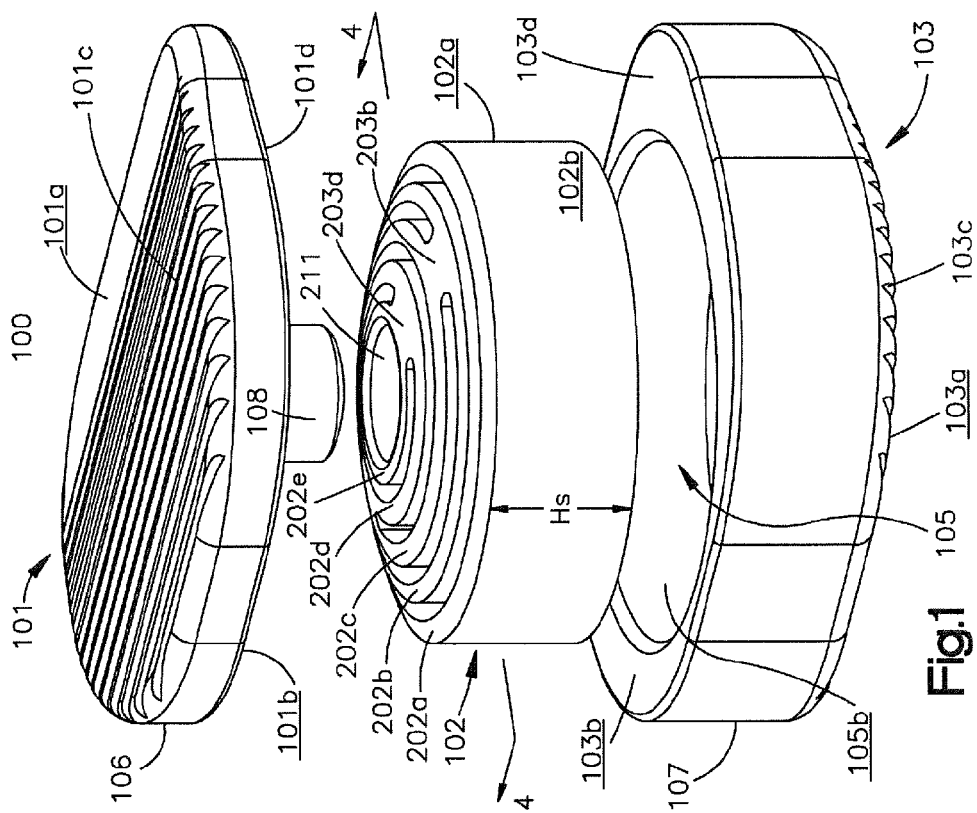

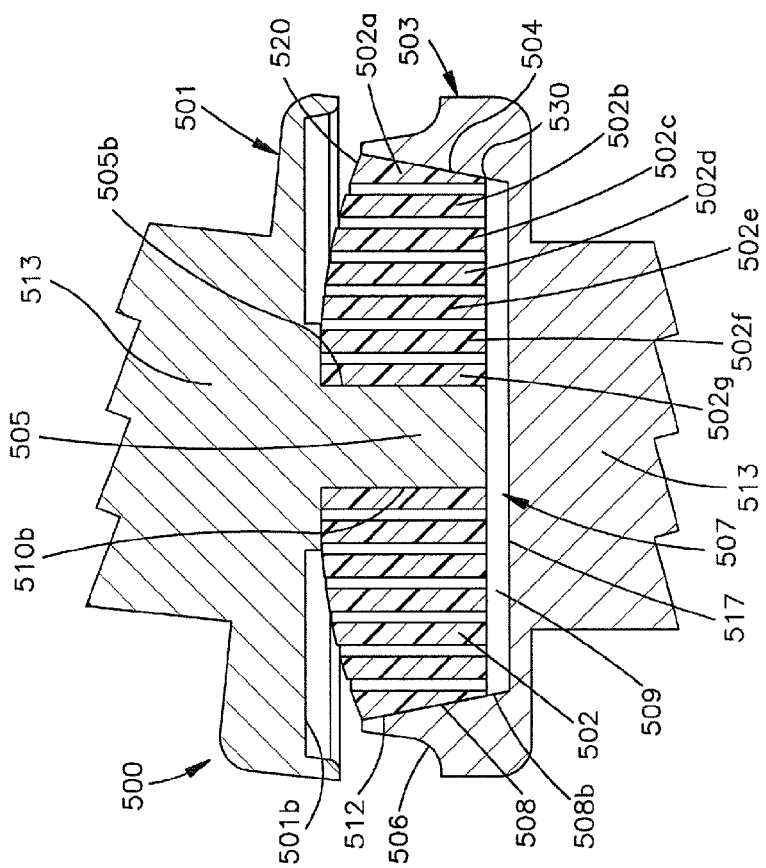
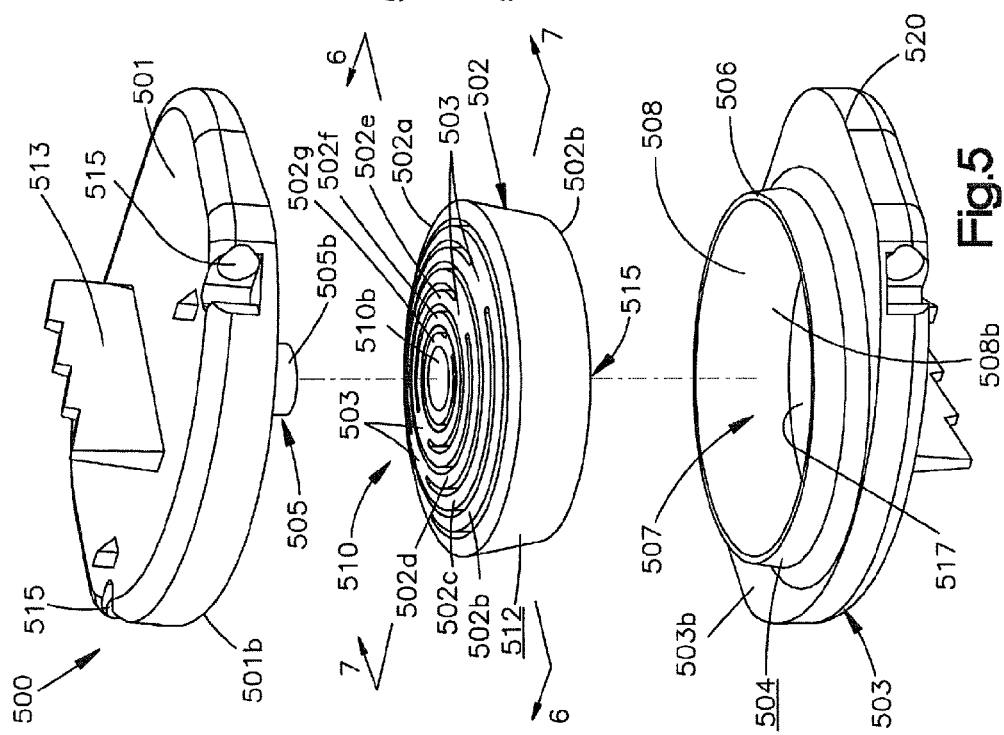

FLEXIBLE DAMPENING INTERVERTEBRAL SPACER DEVICE

CROSS-REFERENCE TO RELATED APPLICATIONS

This application is the National Stage of International Application No. PCT/US2009/050597, filed Jul. 14, 2009, which claims the benefit of U.S. Provisional Application No. 61/080,497, filed Jul. 14, 2008, the disclosures of which are incorporated herein by reference in their entireties for all purposes.

FIELD OF THE INVENTION

This invention relates to an implant, more specifically a joint prosthesis, more specifically an intervertebral implant, and even more specifically a joint prosthesis to replace a spinal disc.

BACKGROUND OF THE INVENTION

Intervertebral spinal discs lie between adjacent vertebrae in the spine. Each disc forms a cartilaginous joint allowing slight movement of the vertebrae and acting as a ligament to hold the vertebrae together. Due to general wear and tear, spinal discs can become damaged or dislocated giving rise to a problem commonly referred to as a "slipped disc." In the past, damaged or diseased discs were treated by removing the disc and packing the space with bone chips to promote fusion of the adjacent vertebrae. However, this method resulted in a loss of mobility in the patient's back. Another solution for treating damaged or diseased discs is to replace the damaged disc with a prosthetic disc implant. However, current prosthetic disc implants generally do not replicate the ranges of motion undertaken by healthy spinal vertebrae and/or contain moving parts that result in wear and possible debris. Thus, it is desirable to develop a prosthetic disc implant that can more closely approximate and permit the ranges of motion typically experienced by healthy spinal segments, without the wear and friction caused by parts moving along other surfaces.

BRIEF SUMMARY OF THE INVENTION

The present invention is related to an implant, more particularly a joint prosthesis, more preferably an intervertebral implant or joint prosthesis to replace a spinal disc. The intervertebral implant in a first embodiment may be a spacer for placement between an upper and lower vertebrae, comprising an upper endplate and a lower endplate. Each endplate may have an outside surface configured and adapted to contact and engage one of the first or second vertebrae. The spacer preferably further includes at least one articulation element having a plurality of segments separated by at least one space, and at least one bridging element connecting adjacent segments. The articulation element may include an innermost segment interposed inside an outermost segment, and optionally one or more intermediate segments. A first portion of the articulation element preferably is operatively associated with one of the upper and lower endplates, and a second different portion of the articulation element preferably is operatively associated with the other one of the upper and lower endplates to permit relative movement of the endplates by flexing of the articulation element without opposed surfaces rubbing against each other. The spacer device preferably provides frictionless, or near frictionless movement between the endplates.

A second embodiment of the present invention may be an intervertebral spacer for placement between an upper and lower vertebrae, comprising an upper endplate and lower endplate, each endplate having an outer surface and an inner surface, the outer surface configured and adapted to contact and engage one of the first and second vertabrae, and the inner surface having a recess. The spacer may further comprise a first intermediate member and a second intermediate member, with at least a portion of the first intermediate member received in the recess of one of the upper and lower endplates and at least a portion of the second intermediate member received in the recess of the other of the upper and lower endplates. The spacer may further comprise at least one articulation element having a plurality of segments separated by at least one space and at least one bridging element connecting the segments. The articulation element may include an innermost segment interposed inside an outermost segment, and optionally one or more intermediate segments. A first portion of the articulation element may be operatively associated with one of the first and second intermediate members, and a second different portion of the articulation element may be operatively associated with the other one of the first and second intermediate members to permit relative movement of the endplates by flexing of the articulation element without opposed surfaces rubbing against each other.

The spacer may further comprise interposed segments that are concentric O-shaped rings. The spacer may further comprise moveable endplates wherein the segments elastically deflect relative to each other when the endplates move relative to each other and/or the bridging elements may elastically deflect when the endplates move relative to each other. The articulation element may provide at least six degrees of motion, including flexion, extension, lateral bending, axial rotation, horizontal shifting, and axial compression.

The height of each of the segments may range from about three (3) mm to about ten (10) mm, the width of each of the segments may range from about five tenths (0.5) of a millimeter to about two (2) mm, and the width of each of the bridging elements may range from about one (1) mm to about ten (10) mm. Other dimensions for the articulation elements, the segments, and the bridging elements are contemplated. The bridging elements and/or segments may connect, preferably flexibly connect, the articulation element to one of the upper and lower endplates. The outermost segment may be fixedly connected to one of the lower and upper endplates and the innermost segment may be fixedly connected to the other one of the lower and upper endplates. The segments may be fixedly connected to their respective endplate by at least one of the group comprising welding, gluing, press fitting and bonding. The articulation element, end plates and intermediate element may be constructed of at least one of the group consisting of a biocompatible metal, Titanium, Titanium alloy, Cobalt-Chromium alloy, a biocompatible polymer, a biocompatible mixture of polymers, Nitinol, shape memory material, ceramic, and a composite material.

The spacer device may have a vertical axis, and the height of each adjacent segment along the vertical axis may increase from the outermost segment towards the innermost segment. Alternatively, the height of each adjacent segment along the vertical axis may decrease from the outermost segment towards the innermost segment. Alternatively, the spacer may have a vertical axis, and the positioning of the ends of adjacent segments may alternate up and down along the vertical axis, forming a zig-zag configuration.

The intervertebral spacer may further have a gapped area between the articulation element and at least one of the endplates to permit the segments to move into this gapped area. One of the endplates of the spacer may include a recessed portion for receiving the articulation element, a raised lip for receiving the articulation element, an inner wall defining the recessed portion, with the inner wall angled in an outwardly direction toward the perimeter of the lower endplate. The outermost segment of the articulation element may have an outer surface forming an angle that protrudes inwardly from the top to the bottom of the articulation element. The outwardly angled inner wall or raised lip of the recessed portion may be configured to receive and contact the inwardly protruding outer surface of the outermost segment.

The intervertebral spacer may further have an optional pin element operatively associated with at least one of the endplates or intermediate members, and received within the space defined by adjacent segments of the articulation element. The pin element may be received within a center space defined by the innermost segment. The pin element may be fixedly connected to one of the endplates or intermediate members and extend toward the other endplate or intermediate member and may be press fit into the center space. Alternatively, the pin element may be loosely received in at least one of the spaces separating the segments of the articulation elements. At least one of the endplates or intermediate members further comprise at least one hole configured for removing manufacturing process debris.

Additionally, the upper endplate, lower endplate, and articulation element may be monolithically formed from a single body of material. The first and second intermediate members, and the articulation element also may be monolithically formed from a single body of material. The spacer may further comprise a second articulation element having a plurality of segments each separated by at least one space and at least one bridging element connecting the adjacent segments. The spacer may further comprise a central shaft element vertically connecting the articulation elements together. The central shaft element may be fabricated from the same body of material as the upper endplate, lower endplate, first intermediate member, second intermediate member, or first and second articulation elements.

Additionally, an elastomer element may fill gaps and spaces between the upper and lower endplates, and act as a load sharing component. Additionally, the spacer may further have at least one vertebral attachment means operatively associated with at least one of the upper and lower endplates comprising at least one from the group of keels, teeth, ridges, spikes, and screws. Additionally, the spacer may further have at least one hole in one of the upper and lower endplates for receiving a fastening member.

The first embodiment of the present invention may further include a method to treat a damaged or diseased spinal disc comprising the steps of: (a) forming an access portal to the damaged or diseased disc; (b) removing at least a portion of a damaged or diseased spinal disc; (c) providing an articulating spacer comprising an upper endplate and lower endplate, and at least one articulation element, the articulation element having a plurality of segments separated by at least one space, and at least one bridging element connecting the segments, the articulation element including an innermost segment interposed inside an outermost segment, wherein a first portion of the articulation element may be operatively associated with one of the upper and lower endplates, and a second different portion of the articulation element may be operatively associated with the other of the upper and lower endplates to permit relative movement of the upper and lower endplates by flexing of the articulation element without opposed surfaces rubbing against each other; and (d) implanting the spacer between the vertebrae.

The second embodiment of the present invention may further include a method of treating a damaged or diseased spinal disc comprising the steps of: (a) forming an access portal to the damaged or diseased disc; (b) removing at least a portion of a damaged or diseased spinal disc; (c) providing at least two endplates for attaching to a vertebrae, each endplate having a recess; (d) implanting each endplate into adjacent vertebrae; (e) providing a core assembly comprising a first and second intermediate member, and at least one articulation element having a plurality of segments, separated by at least one space, and at least one bridging element connecting the segments, the articulation element including an innermost segment interposed inside an outermost segment, wherein a first portion of the articulation element may be operatively associated with one of the first and second intermediate members, and a second different portion of the articulation element may be operatively associated with the other of the first and second intermediate members to permit relative movement of the intermediate members by flexing of the articulation element without opposed surfaces rubbing against each other; and (f) inserting the core element into the endplates.

The method of treating a damaged or diseased spinal disc may further include inserting the core assembly by sliding the first intermediate member into the recess of one of the endplates and sliding the second intermediate member into the recess of the other endplate. The method may further include fixedly joining the core assembly to the endplates.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the preferred intervertebral implant and/or spine prosthesis of the present application, drawings of the preferred embodiments are shown. It should be understood, however, that the application is not limited to the precise arrangement, structures, features, embodiments, aspects, and instrumentalities shown, and the arrangements, structures, features, embodiments, aspects and instrumentalities shown may be used singularly or in combination with other arrangements, structures, features, embodiments, aspects and instrumentalities. In the drawings:

FIG. 1 is a side perspective, exploded view of a first preferred embodiment of an intervertebral spacer device in accordance with the present invention;

FIG. 2 is a top plan view of the articulation element and lower endplate of the intervertebral spacer device of FIG. 1;

FIG. 5 is a side perspective, exploded view of a second preferred embodiment of the intervertebral spacer device of the present invention;

FIG. 6 is a cross-sectional view of the intervertebral spacer device of FIG. 5 taken along line 6-6 of FIG. 5 in an assembled configuration;

DETAILED DESCRIPTION OF THE INVENTION

Figure 3:
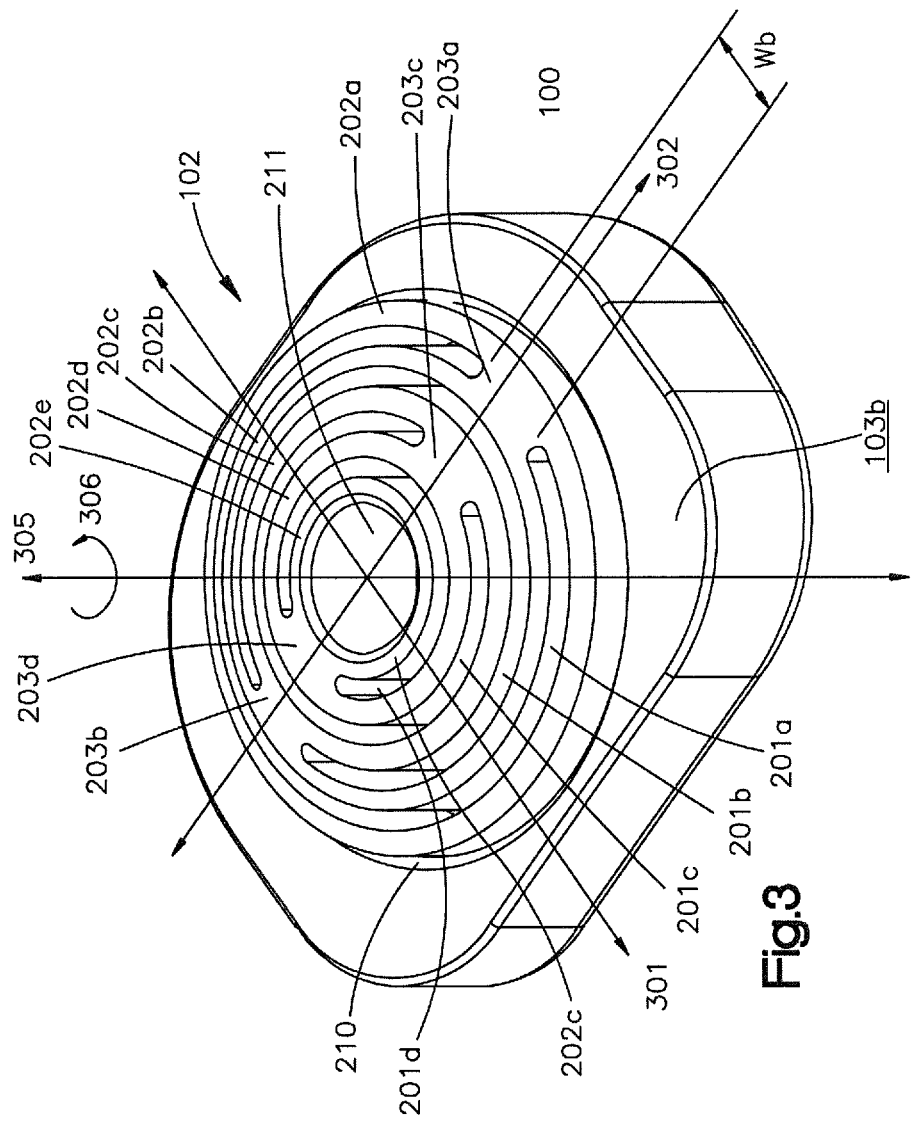
FIG. 3 is a top perspective view of the articulation element and lower endplate of the intervertebral spacer device of FIG. 1 illustrating the motions permitted in the horizontal plane.

Certain terminology is used in the following description for convenience only and is not limiting. The words "right", "left", "lower", "upper", "top", and "bottom", designate directions in the drawings to which reference is made. The words "inwardly" or "distally" and "outwardly" or "proximally" refer to directions toward and away from, respectively, the geometric center of the intervertebral spacer device and related components and are not meant to be limiting. The words, "anterior", "posterior", "superior", "inferior", "lateral" and "medial" and related words and/or phrases designate preferred positions and orientations in the human body to which reference is made and are not meant to be limiting. The terminology includes the above-listed words, derivatives thereof and words of similar import.

Figure 14:
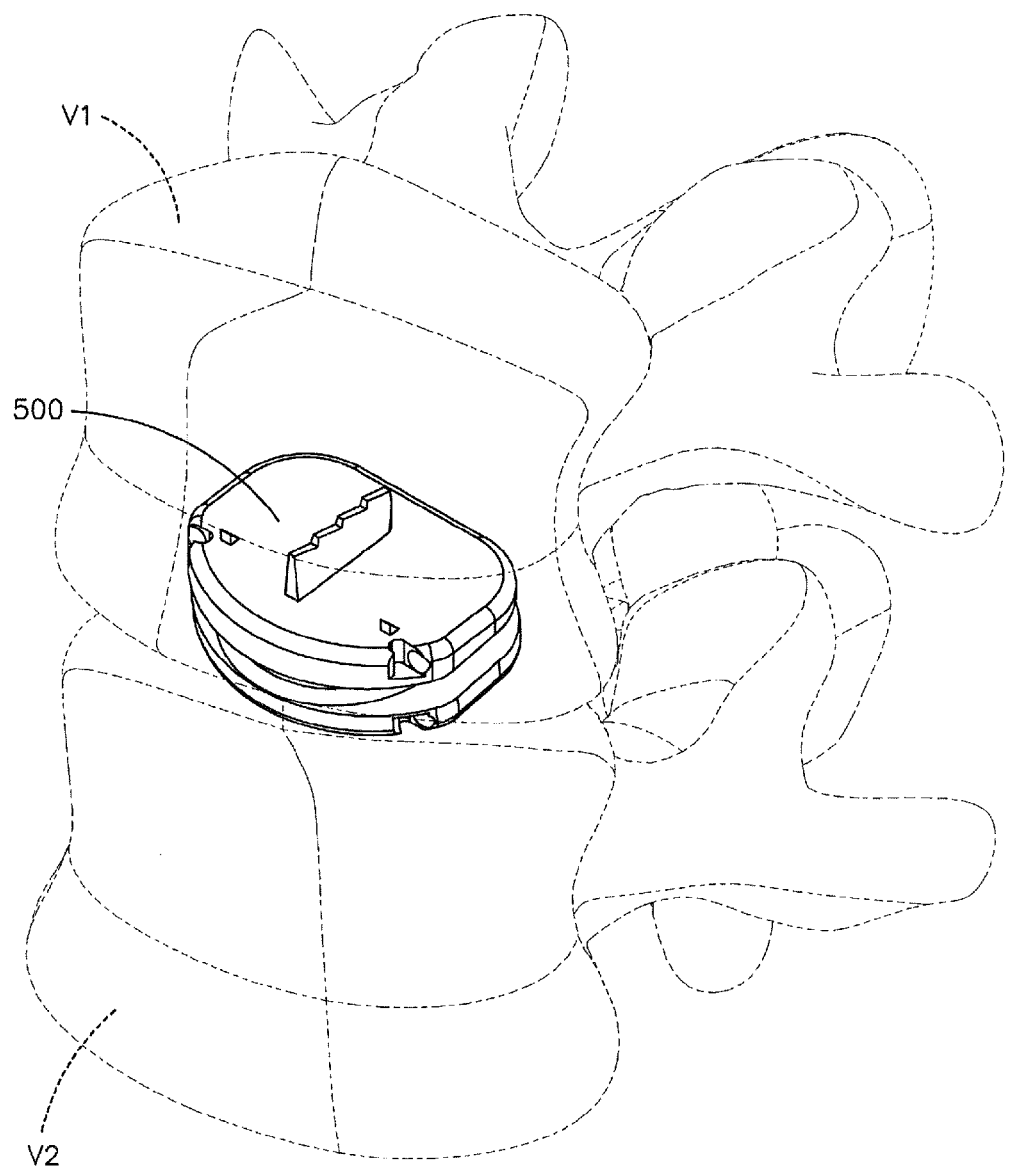
FIG. 14 is a top perspective view of the intervertebral spacer device positioned in the spine between adjacent superior and inferior vertebrae.

FIGS. 1-4 illustrate a first preferred embodiment of an articulating intervertebral spacer device 100. The spacer 100 is preferably used in the spine, and may be used in the cervical, thoracic, and/or lumbar regions of the spine. While the spacer 100 is described as generally for use in the spine, those of ordinary skill in the art will recognize that the spacer 100 may have other uses and may be used as a prosthesis for other joints, such as, for example, the shoulder, elbow, wrist, hip, knee, ankle, toe and finger. FIG. 14 illustrates a preferred use of the spacer device 500 implanted in the spine, in between adjacent superior vertebrae 25 and inferior vertebrae 50. Although FIG. 14 shows spacer 500, any of the spacers 100, 500, 700, 800, and 900 may preferably be used in between adjacent vertebrae in this manner. Moreover, generally throughout the application, various embodiments of the spacer may be referred to by reference numerals 100, 500, 700, 800, and 900.

The spacer 100 of the first preferred embodiment preferably allows at least six degrees of freedom of motion, with minimal or no friction between moving parts. The six degrees of motion include flexion, extension, lateral bending, axial rotation, horizontal shifting, and axial dampening, as well as combinations of each. One advantage provided by relative motion with little or no friction is that little or no wear is generated by rubbing parts and, hence, little or no debris or extraneous material is created during operation of the spacer 100.

In the spine, flexion is when the spinal column undergoes the act of bending forward in an anterior direction, such as, for example, when a person bends forward, such as to look at their toes. Extension is when the spine undergoes the act of bending back in a posterior direction, such as, for example, when a person bends backwards, such as to look at the sky. Axial rotation is when the spine undergoes a rotary motion about its vertical axis, such as, for example, when a person twists their body about the vertical axis of the spine. Lateral bending is when the spine undergoes the act of bending side to side, i.e., in a medial or lateral direction (orthogonal to an anterior or posterior direction). Horizontal shifting is when the axis of rotation of the vertebrae in the spine translates laterally. Horizontal shifting may occur in the anterior and posterior directions, as well as the medial and lateral directions, and combinations thereof.

Axial compression occurs when the spine is loaded in the vertical direction which compresses the spinal discs in the spine. Axial compression occurs when a person connects with the ground, such as, for example, when walking, running, jumping, etc. Spinal discs absorb these axial compressive forces which is referred to as axial dampening.

In instances where a cartilaginous spinal disc becomes damaged, or in the case of diseased spinal discs, a surgeon may perform a partial or complete discectomy and implant the spacer 100, preferably to mimic the type and degree of motion and dampening capabilities of natural, healthy, spinal discs. As shown in FIGS. 1-4, the spacer 100 includes an upper plate 101, a lower plate 103, and an articulation element 102, with the articulation element 102 situated between the upper plate 101 and lower plate 103. The spacer 100 is designed so that, in situ, the upper plate 101 moves relative to the lower plate 103, preferably with little or no friction. Preferably, the spacer 100 has no elements that rub together or move along each other and thus little or no friction is generated by movement of the parts and preferably little or no wear debris is created. The upper plate 101 and lower plate 103, are operatively associated with one another by the articulation element 102, and preferably are configured to form a joint prosthesis to partially or fully replace a disc between two adjacent vertebrae. The upper plate 101 preferably does not contact or impinge on the lower plate 103, and instead, the upper plate 101 is separated from the lower plate 103 by the presence of the articulation element 102. Although the upper and lower plates 101, 103 move relative to the position of each other, they are operatively associated with, and preferably fixedly attached to portions of the articulation element 102, creating an articulating, generally frictionless or near frictionless body. The upper and lower plate 101, 103 of spacer 100 are permitted to move relative to each other because of the flexibility and ability of the articulation element 102 to elastically deflect.

The upper and lower plates 101, 103 of the spacer 100 preferably are configured as endplates and preferably have an outer surface 101a, 103a configured for operative association and preferably attachment to adjacent superior and inferior vertebrae located in the spine. The outer surfaces 101a, 103a may be relatively smooth. Alternatively, or in addition to, the outer surfaces 101a, 103a may be textured or have portions that are textured, such as ridges 101c, 103c, to facilitate engagement and attachment to the vertebrae. Additionally and/or alternatively, the outer surfaces 101a, 103a may have vertebral attachment elements such as keels, teeth, ridges, porous structures for bone in-growth, or other attachment means now known, or later discovered.

The upper and lower plates 101, 103 may have outer surfaces that are curved, relatively flat, and/or inclined to assist in maintaining the curvature and/or alignment of the vertebrae in the spine, and the desired shape of the upper and lower plates 101, 103, as relatively flat, curved, or inclined will depend upon the location of the spacer 100 in the spine and the condition of the spine. The upper and lower plates 101, 103 of the spacer 100 may have an outer perimeter 106, 107 which may be kidney shaped, or generally "D" shaped, as shown, or may take on other exemplary shapes, such as, for example, circular, rectangular, octagonal, triangular, oval, etc. The outer surfaces 101a, 103a are preferably shaped to contact as much of an endplate of the vertebrae that the spacer 100 is mounted between in an implanted configuration.

The upper and lower plates 101, 103 of the spacer 100 preferably also have an inner surface 101b, 103b which preferably may be relatively flat and/or have a relatively flat portion or portions 101d, 103d. The upper and lower plates 101, 103 may be of any suitable thickness. Preferably, the articulation element 102 is operatively associated with, and more preferably fixedly attached to, the inner surfaces 101b, 103b of both upper and lower plates 101, 103, preferably to the inner surfaces 101b, 103b.

The spacer 100 preferably has an outer perimeter 104 that may be of any suitable shape, including, but not limited to, circular, rectangular, oval, triangular, octagonal, "D" shaped, or kidney shaped. The outer perimeter 104 of the spacer 100 may be defined by the outer perimeter 106, 107 of the upper and lower plates 101, 103, respectively. The spacer 100 may be dimensioned and sized to provide the optimal size and properties desired for the specific application.

In the first preferred embodiment preferably for use in the lumbar region of the spine, the spacer 100 is "D" shaped, or kidney shaped, having a width $W_t$ preferably ranging from approximately twenty (20) mm to approximately thirty (30) mm, more preferably about twenty four (24) mm to about twenty six (26) mm, more preferably about twenty five (25) mm. The spacer 100 of the first preferred embodiment, preferably has a length $L_t$ ranging from approximately seventeen (17) mm to approximately twenty four (24) mm, more preferably about nineteen (19) mm to about twenty one (21) mm, more preferably about twenty (20) mm. The spacer 100 may preferably have a height $H_t$ ranging from approximately three (3) mm to approximately seven (7) mm, more preferably about five (5) mm to about six (6) mm. Other dimensions, including but not limited to the dimensions for the length, width, depth, and height of the spacer 100 described above are contemplated for the spacer.

In a preferred embodiment preferably for use in the cervical region of the spine, the spacer 100 may have a width $W_t$ preferably ranging from approximately fifteen (15) mm to approximately nineteen (19) mm, and a length $L_t$ ranging from approximately twelve (12) mm to approximately eighteen (18) mm. Other dimensions, including but not limited to the dimensions for the length, width, depth, and height of the spacer 100 described above are contemplated for the spacer.

Articulation element 102 preferably includes one or more segments 202, preferably interposed segments, preferably concentric segments, separated by spaces or gaps 201 and connected by one or more bridging elements 203. Preferably, the segments 202 have increasing or decreasing inner and outer perimeters (for example, inner and outer perimeter of outer segment 205a, 205b), allowing the segments 202 to fit interposed between one another. The segments 202 preferably are separated by spaces or gaps 201 located between segments 202, preferably permitting relative movement of the segments 202. The bridging elements 203 preferably connect one or more segments 202 to each other, and preferably connect adjacent segments 202. The bridging elements 203 may also connect to the upper or lower plates 101, 103. The spaces 201 preferably are defined and bounded by the segments 202 and bridging elements 203. The segments 202 are preferably arranged and configured to be flexibly connected by the bridging elements 203 which are preferably flexible and elastically deflectable to permit movement of the segments 202 relative to each other. In addition the segments 202 themselves may be flexible and elastically deflectable. The articulation element 102 preferably forms a flexible core assembly.

In the first preferred embodiment, the articulation element 102 is constructed of a Cobalt-Chromium alloy, and the upper and lower plates 101, 103 are constructed of Titanium or biocompatible Titanium alloy. In another embodiment, the articulation element 102 may be constructed of the same material as the upper and lower plates 101, 103. The articulation element 102, and/or the upper and lower plates 101, 103 may be made of any biocompatible metal, metal alloy, polymer, mixture of polymers, Nitinol, shape memory alloy, ceramic, or composite material. The segments 202 may be constructed of different material than the bridging elements 203.

In the first preferred embodiment, five concentric segments 202a-e, are connected by four bridging elements 203a-d. The segments 202 are continuously closed shapes, i.e., the segments 202 form a closed space, and preferably the segments 202 are shaped as closed rings or "O" shaped rings. The segments 202, however, may be of any shape, including, but not limited to, circular, rectangular, oval, "C" shaped, horseshoe, triangular, octagonal, or kidney shaped. The articulation element 102 in the embodiment of FIGS. 1-4 has an outer segment 202a, intermediate segments 202b-d, and an inner segment 202e. Intermediate spaces 201a-d surround the intermediate segments 202b-d, and an inner or center space 211 is located inside the inner segment 202e. The number of segments 202, spaces 201, and bridging elements 203 may vary and are not limited to any particular number, value or range. Although FIG. 2 illustrates an embodiment with closed concentric segments 202, the segments 202 may also be "open," forming, for example, a "C-shaped" segment, horseshoe shaped, or any other suitable shape.

The inner surface 103b of the lower plate 103 preferably has a recessed portion 105 for receiving and accommodating the articulation element 102. The articulation element 102 may be operatively associated with and preferably attached, and preferably fixedly attached, to the wall 105b of the lower plate 103. The articulation element may be press-fit, welded, electron beam welded, bonded, or fastened to the lower plate 103, and any other joining mechanism or means now known or later discovered may be used to join the articulation element to the lower plate 103. More specifically, a lower portion 102b of an outer surface 102a of the outer segment 202a of the articulation element 102 may preferably have substantial contact with a wall 105b of the recessed portion 105. Preferably, the lower portion 102b of the outer surface 102a of the outer segment 202a of the articulation element 102 may be attached to the recessed portion 105 to leave a space or gap 109 between the bottom surface 111 of the articulation element 102 and the bottom surface 110 of the lower plate 103 such that the segments 202 of the articulation element 102 preferably float above the bottom surface 110 of the recessed portion 105.

The articulation element 102 may also be operatively associated with and preferably attached to the upper plate 101. The top surface of at least one of the segments 202a-e or bridging elements 203a-d may preferably be attached, preferably fixedly attached, to the inner surface 101b of the upper plate 101. The articulation element may be press-fit, welded, electron beam welded, bonded, or fastened to the upper plate 101, and any other joining mechanism or means now known or later discovered may be used to join the articulation element 102 to the upper plate 101. Preferably, the inner segment 202e of the articulation element 102 may be attached, preferably fixedly attached, to the inner surface 101b of the upper plate 101. In one embodiment, the upper surface 202f of the inner segment 202e is fixedly attached to the upper plate 101 preferably by welding. In an alternative embodiment, an optional pin element 108 may extend from the inner surface 101b of the upper plate 101, toward the lower plate 103 and into the inner space 211 of the articulation element 102. Additionally, and/or alternatively, the pin element 108 may be located in spaces 201 between adjacent segments 202. The pin element 108 is attached to the articulation element 102 preferably in a manner that allows forces to be transmitted from adjacent vertebrae to the upper and lower plates 101, 103, and to the articulation element 102. The optional pin element 108 may be press fit into the inner space 211 to fixedly attach the articulation element 102 to the upper plate 101. Other attachment and joining means, as described above, for joining the pin element 108 to the inner segment 202c may be used.

Additionally and/or alternatively, the pin element 108 may have no connection with the articulation element 102, and may fit loosely in the inner space 211 or other spaces 201 so that the pin element 108 can move within the inner space 211 or other spaces 201. As the pin element 108 moves in the inner space 201c and contacts the inner segment 202c, the pin can transfer forces from the upper plate 101 to the articulation element 102.

When forces are applied to the upper and lower plates 101, 103, the articulating element 102 preferably responds with relative movement of the segments 202. When forces are applied, the segments 202, and/or bridging elements 203 elastically deflect and move relative to each other. For example, when lateral bending is applied to the upper and lower plates 101, 103, the portion of the segments 202 on the side of the articulation element 102 where force was applied will move closer to one another, narrowing the spaces 201 between them, and the portion of the segments 202 on the opposing side will move farther apart from one another, widening the spaces 201 between them. The segments 202 preferably move frictionless with respect to each other, and the upper and lower plates 101, 103.

Figure 4:
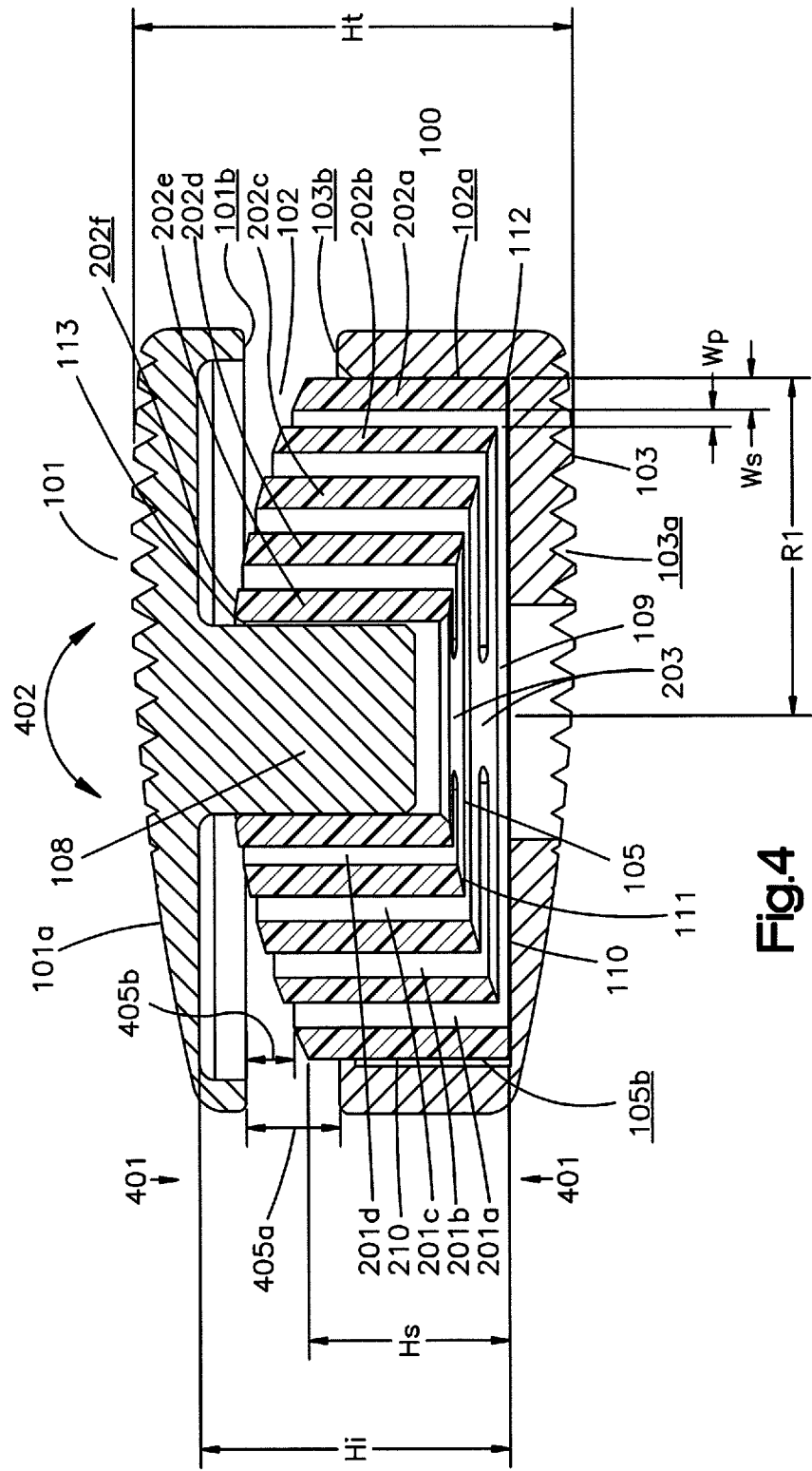
FIG. 4 is a cross-sectional view taken along line 4-4 of FIG. 1 of the intervertebral spacer device of FIG. 1 in an assembled configuration illustrating the motions permitted in the saggital plane.

The segments 202 preferably allow for movement in at least six degrees of motion, including flexion, extension, lateral bending, axial rotation, horizontal shifting, and dampening, as described above. FIG. 4 illustrates a cross sectional view of the spacer 100, where upper and lower plates 101, 103 move relative to the articulation element 102 allowing flexion and extension. Upper and lower plates 101, 103 may also move in a lateral/medial direction (not shown) relative to the articulation element 102. The segments 202 and bridges 203 may also provide dampening against compressive forces along a vertical axis 305. Accordingly, when compressive forces are applied to the upper and lower plates 101, 103, the segments 202 can translate in the axial direction, or deflect in the direction of the applied force. The space 105 below the articulation element 102 allows the segments 202 to translate preferably without contacting the bottom surface 110 of the recessed portion 105. Additionally, and/or alternatively, the bridging elements 203 can deflect upon application of force. The deflection and translation of the segments 202 and bridging elements 203 in response to compressive forces creates a dampening effect in the spacer 100.

When the spacer 100 is designed for use in the lumbar region of the spine, the spacer 100 preferably allows for the spine to experience the following ranges of motion: (i) about +/−10 degrees during flexion and extension, (ii) about +/−7 degrees during lateral bending, and (iii) about +/−10 degrees during axial rotation.

The bridging elements 203 of the first preferred embodiment connect the segments 202 and may permit and provide resistance to relative movement of the segments 202, and the upper and lower plates 101, 103. The resistance to relative movement of the segments 202, and consequently the upper and lower plates 101, 103, may be varied and controlled by altering the number, height, material, thickness (or width), shape, or other properties of the segments 202. The resistance to relative movement of the segments 202 and consequently the upper and lower plates 101, 103 also may be varied and controlled by altering the number, width, thickness, material, shape, or other properties of the bridging elements 203. Resistance to the relative movement of the segments 202, and consequently the upper and lower endplates 101, 103, may also be varied and controlled by increasing the number of bridging elements 203 that connect two segments 202. Multiple bridging elements 203 may be used to connect adjacent segments 202 to vary the resistance to relative movements between the segments 202. Although the first preferred embodiment of the spacer 100 includes bridging elements 203 aligned along a medial/lateral axis 302 (i.e., orthogonal to the anterior/posterior axis 301), the bridging elements 203 may be positioned in any manner desirable between the segments 202 of the articulation element 102. When positioned in an aligned fashion, as shown, the bridging elements 203 generally preferably provide a symmetrical response to applied forces, and may provide stiffer resistance in the direction of alignment. If an application where non-symmetrical responses is desired, the positioning of the bridging elements 203 may be altered accordingly.

The articulation element 102 may preferably be circular in shape as shown in FIG. 2, having a total radius R preferably ranging from approximately seven (7) mm to approximately nineteen (19) mm, more preferably about eleven (11) mm to about thirteen (13) mm, more preferably about twelve (12) mm. The segments 202 may preferably have a width $W_s$ preferably ranging from about five tenths of a millimeter (0.5) mm to about two (2) mm, more preferably about one (1) mm. The bridging elements 203 may preferably have widths $W_b$ ranging from about one (1) mm to about ten (10) mm, more preferably about two (2) mm to about seven (7) mm and a thickness T ranging from about one tenth (0.1) of a millimeter to about one (1) millimeter, more preferably about four tenths (0.4) of a millimeter to about six tenths (0.6) of a millimeter, more preferably about five tenths (0.5) of a millimeter. The spaces 201 may preferably have widths $W_p$ ranging from about one tenth (0.1) of a millimeter to about one (1) mm, more preferably about four tenths (0.4) of a millimeter to about six tenths (0.6) of a millimeter, more preferably five tenths (0.5) of a millimeter. The segments 202 may preferably have a height $H_s$ ranging from about three (3) mm to about ten (10) mm, more preferably, about five (5) mm to about seven (7) mm. It should be noted that these dimensions are only exemplary and other dimensions are contemplated for the articulation element 102, segments 202, bridging elements 203, and spaces 201.

Additionally, a height $H_s$ of the articulation element 102, and the spacer 100 may be different on the anterior side than the posterior side (i.e., along the anterior/posterior axis 301). The height of the articulation element 102, and the spacer 100 may be different on the lateral and medial sides as well (i.e., along the medial/lateral axis 302). Preferably, this may be accomplished by offsetting certain portions of the segments 202 higher or lower than other portions, or by manufacturing the specific segments 202 with a greater height. This allows for a spacer 100 which can specifically accommodate patients taking into account their individual lordosis and individual kyphosis and the condition of the spine being treated.

The articulation element 102 may be constructed of any material, preferably a material that permits for some flexibility. In the first preferred embodiment, the articulation element 102 is constructed of a Cobalt-Chromium alloy. Alternatively, the articulation element 102 may be constructed of Titanium or a biocompatible Titanium alloy, a shape memory material such as Nitinol, or any biocompatible metal, metal alloy, polymer, mixture of polymers, ceramic, composite material, or combination of materials.

The spacer 100 also may preferably have an optional silicone, polyurethane elastomer, or other suitable filler, injected into the spaces in the spacer, to provide load bearing and load sharing capabilities. Alternatively, and/or additionally, a clip (not shown) preferably can be inserted in spacer 100 to restrict or prevent movement of the upper and lower plates 101, 103 and/or articulation element 102.

Limited axial rotation 306 preferably occurs in two directions, clockwise and counterclockwise, about a vertical central axis 305. The presence and flexibility of the bridging elements 203 between the segments 202 limits and resists the ability of full rotation. The articulating element 102 also allows limited horizontal shifting movements of the segments 202, and consequently limited horizontal shifting of the upper and lower plates 101, 103 in the horizontal plane, i.e. limited horizontal shifting along the anterior/posterior axis 301, and medial/lateral axis 302 or shifting along both axes. Both the presence of the bridging elements 203 between the segments 202, as well as wall 105b of the recessed portion 105 for receiving the articulation element 102, permit and/or limit the horizontal shifting motion of the segments when translational forces are applied. Additionally, the bridging elements 203 between the segments 202 may provide resistance to and permit simultaneous axial rotation and horizontal shifting.

In the first preferred embodiment, the spacer 100 preferably has open space 405a, preferably positioned laterally to the side of the articulation element 102, and in between the upper and lower plates 101, 103 preferably so that upper and lower plates 101, 103 do not abut or contact one another when it is implanted and operational in a patient's spine, preferably even when fully articulated, pivoted, rotated, or fully compressed. Preferably, the open space 405a may be achieved by offsetting each of the segments 202a-e in an upwardly vertical axial direction 305, such that the outermost segment 202a is in a lowest position 112, and the innermost segment 202e is in a highest position 113. Vertically offsetting the adjacent segments 202, as shown in FIG. 4, also preferably allows for pivoting and articulation of the upper plate 101 about the articulation element 102, by providing another open space 405b between the segments 202 and the upper plate 101. Additionally, offsetting of the segments 202 in an upwardly vertical axial direction 305 may preferably create a gap 109 in between the articulation element 102 and the lower plate 103. This gap 109 provides space for the segments 202 to move in the axial direction 305 providing for dampening qualities when compression forces are applied to the upper and lower plates 101, 103.

Alternatively, the open space 405b may be achieved by offsetting each of the segments 202a-e in a downwardly vertical direction, such that the outermost segment 202a is in a highest position, and the innermost segment 202e is in a lowest position. In another alternative arrangement, the ends of each segment 202 may be offset with respect to its adjacent segments 202 alternating in upward and downward vertical axial directions (i.e., along the vertical axis 305), such as to form a zig-zag like configuration. Additionally, offsetting of the segments 202 in a zig-zag like configuration may preferably create a gap 105 in between the articulation element 102 and the lower plate 103. This gap 105 provides space for the segments 202 to translate in the axial direction 305 providing for dampening qualities when compression forces are applied to the upper and lower plates 101, 103. As stated above, the resistance and flexibility of the articulation element 102 to movements in any direction may be varied by altering the number, width, height, thickness, materials, or other properties of the various segments 202, spaces 201, and bridging elements 203.

Alternatively, rather than offsetting the segments 202a-202c, the segments 202 may increase or decrease in height $H_s$, providing a similar open space 405b for articulation of the upper and lower plates 101, 103.

Referring to FIG. 5 and FIG. 6 a second preferred embodiment of the spacer 500 includes a lower plate 503 having a recessed portion 507 and a raised lip 506, an upper plate 501, and an articulating element 502. The lower plate 503 includes an inner surface 504 preferably comprising recessed portion 507, preferably for receiving the articulation element 502. The recessed portion 507 is preferably the same as or similar in shape to the articulation element 502. The recessed portion 507 includes an inner wall 508 preferably angled in an outwardly direction toward the perimeter 520 of the lower plate 503. In the second preferred embodiment, the articulation element 502 has an outer surface 512 preferably forming an angle inwardly protruding from top 520 to bottom 530 preferably configured to match the angle of the inner wall 508. The outer surface 512 of the articulation element 502, and consequently, an outer surface 512 of an outer segment 502a, preferably contact the inner wall 508 of the recessed portion 507 along substantially the entire opposed surfaces 512, 508. The size of base 515 of the articulation element 502 is such that it is larger than the size of a base 517 of the recessed portion 507, preferably to prohibit the base 515 of the articulation element 502 from contacting and resting on the base 517 of the recessed portion 507, thus creating a gapped area 509 beneath the articulation element 502 and the base 517. The presence of the gapped area 509 below the articulation element 502 permits the spacer 500 to dampen axial compression. When a compressive force is applied axially to the upper or lower plates 501, 503, this force is transmitted to the articulation element 502 which resists the axial force due to the segments 202 and bridging elements 503. The gapped area 509 preferably allows the intermediate and inner segments 502b-g of the articulation element 502 to move downwardly preferably without contacting the lower endplate 503, thus dampening any compressive force on the plates 501, 503, providing qualities similar to a shock absorber. When the articulation element 502 is assembled in the lower plate 103, the height $H_s$ of the outer segment 502a is preferably flush with a height of the lip portion 506

The spacer 500 of the second preferred embodiment also includes pin element 505 extending from a center region of an inner surface 501b of the upper plate 501. When assembled, the pin element 505 preferably extends toward the lower plate 503 and extends into an inner space 510 of the articulation element 502. The pin element 505, having an outer surface 505b, preferably is operatively associated with and preferably attached, and preferably fixedly attached, to the articulation element 502 at the inner space 510. The diameter of the inner space 510, having an inner wall 510b, may be similar or equivalent to the diameter of the pin element 505, preferably allowing contact, along a substantial portion of opposing surfaces 505b, 510b of the pin element 505 and inner space 510. The pin element 505 preferably does not extend into the gapped area 509 and preferably does not contact the lower endplate 503 at the base 517. Additionally, when the spacer 500 is placed into the spine and subject to compressive forces in the spine, the pin element 505 preferably does not contact base 517. Although articulation element 502 of the second preferred embodiment includes a cylindrical inner space 510 and pin element 505, the inner space 510 and pin element 505 may be constructed of nearly any shape. For example, the pin element 505 may be fabricated out of one piece that includes the upper plate 501 or may be attached to the upper plate 501 by press-fit, welding, bonding, use of fasteners, or any other joining mechanism or means now known or later discovered. The pin element 505 may also be attached to the inner segment 502g of the articulation element 502 by press-fit, welding, bonding, use of fasteners, or any other joining mechanism or means now known or later discovered. Additionally, the pin element 505 need not be attached at all, and may fit loosely within the inner segment 502g. Further, the pin element 505 may be bayonet locked to the articulation element 502 and take on a variety of shapes, such as "L" shaped, hexagonal shaped, rectangular shaped, and any shape that permits engagement to the articulation element 502.

The upper and lower plate 501, 503 of the preferred embodiment further include a keel 513, preferably for enhancing stability of the attachment of the upper and lower plate 501, 503 to adjacent vertebrae (not shown). The keel 513 may be fabricated out of one piece that includes the upper or lower plates 501, 503, or may be attached to the upper or lower plates 501, 503 by press-fit, welding, bonding, use of fasteners, or any other joining mechanism or means now known or later discovered. Additionally, and/or alternatively, the upper and lower plates 501, 503 may include other vertebral attachment means such as teeth, spikes, screws, or any other attachment mechanism or means now known or later discovered. Additionally, holes 515 for engaging the plates 501, 503 with an instrument may be provided on either or both plates 501, 503 for translating, removing, or otherwise manipulating the spacer 500. The spacer 500 also may preferably have a silicone, polyurethane elastomer, or any other suitable filler, injected into spaces and gaps in the spacer 500, to provide load bearing and load sharing capabilities. Additionally, a clip (not shown) preferably can be inserted in spacer 500 to restrict movement of the upper and lower plates 501, 503 and/or articulation element 502.

Figure 7:
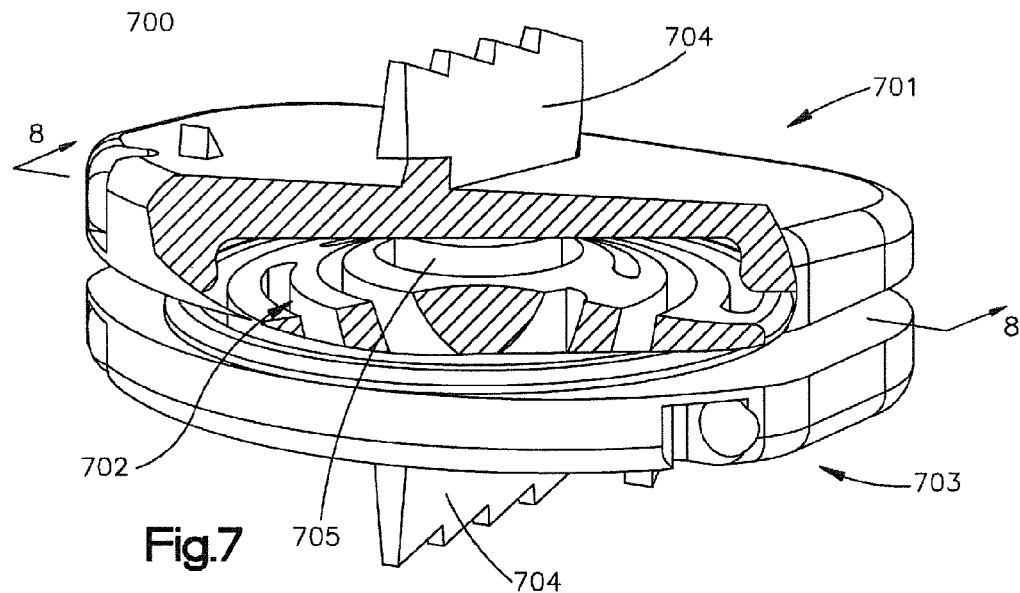
FIG. 7 is a side perspective, partial cross-sectioned view of an intervertebral spacer device in accordance with a third preferred embodiment of the present invention.
Figure 8:
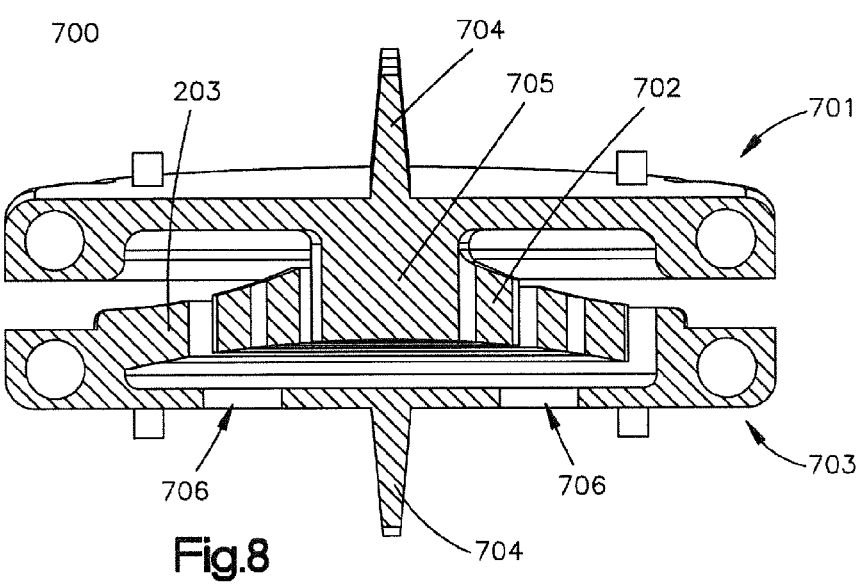
FIG. 8. is a cross-sectional view of a the intervertebral spacer device of FIG. 7, taken along line 8-8 of FIG. 7.

Referring to FIG. 7 and FIG. 8, a third preferred embodiment of an intervetebral spacer 700 includes an upper plate 701 having an articulation element 702, pin element 705, a keel element 704, and a lower plate 703. The pin element 705 is attached to, connected to and forms part of the innermost segment 202e whereas the bridging element 203 connects the outermost segment 202a to the lower endplate 703 The upper and lower plates 701, 703 are preferably fabricated out of one piece of material. This may be achieved, for example, by selective laser sintering (SLS) or selective laser melting (SLM), or by any other fabrication techniques now known or later discovered. Holes 706 may be provided in the upper or lower plates 701, 703 in order to allow for the removal of surplus material inherent to the fabrication technique. The spacer 700 of the third preferred embodiment further includes an articulation element 702 that permits relative movement of the plate 701, 703, similar to the articulation element 102, 502 of the first and second preferred embodiments. The spacer 700 also may preferably have a silicone, polyurethane elastomer, polycarbonate urethane (PCU), or any other suitable filler, injected into spaces and gaps in the spacer 700, to provide load bearing and load sharing capabilities. Additionally, a clip (not shown) preferably can be inserted in spacer 700 to restrict movement of the upper and lower plates 701, 703 and/or articulation element 702.

Figure 9:
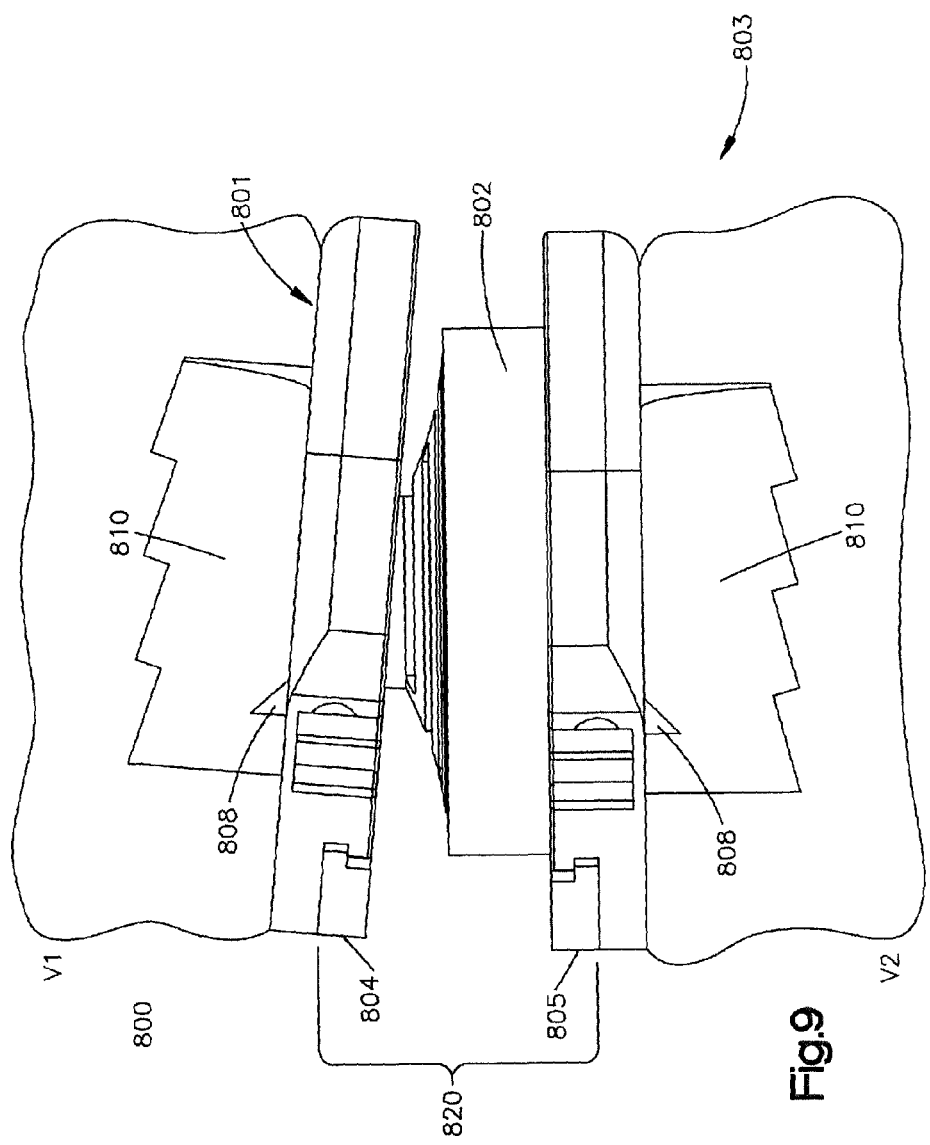
FIG. 9 is a side elevational view of a fourth preferred embodiment of the intervertebral spacer device of the present invention.
Figure 10:
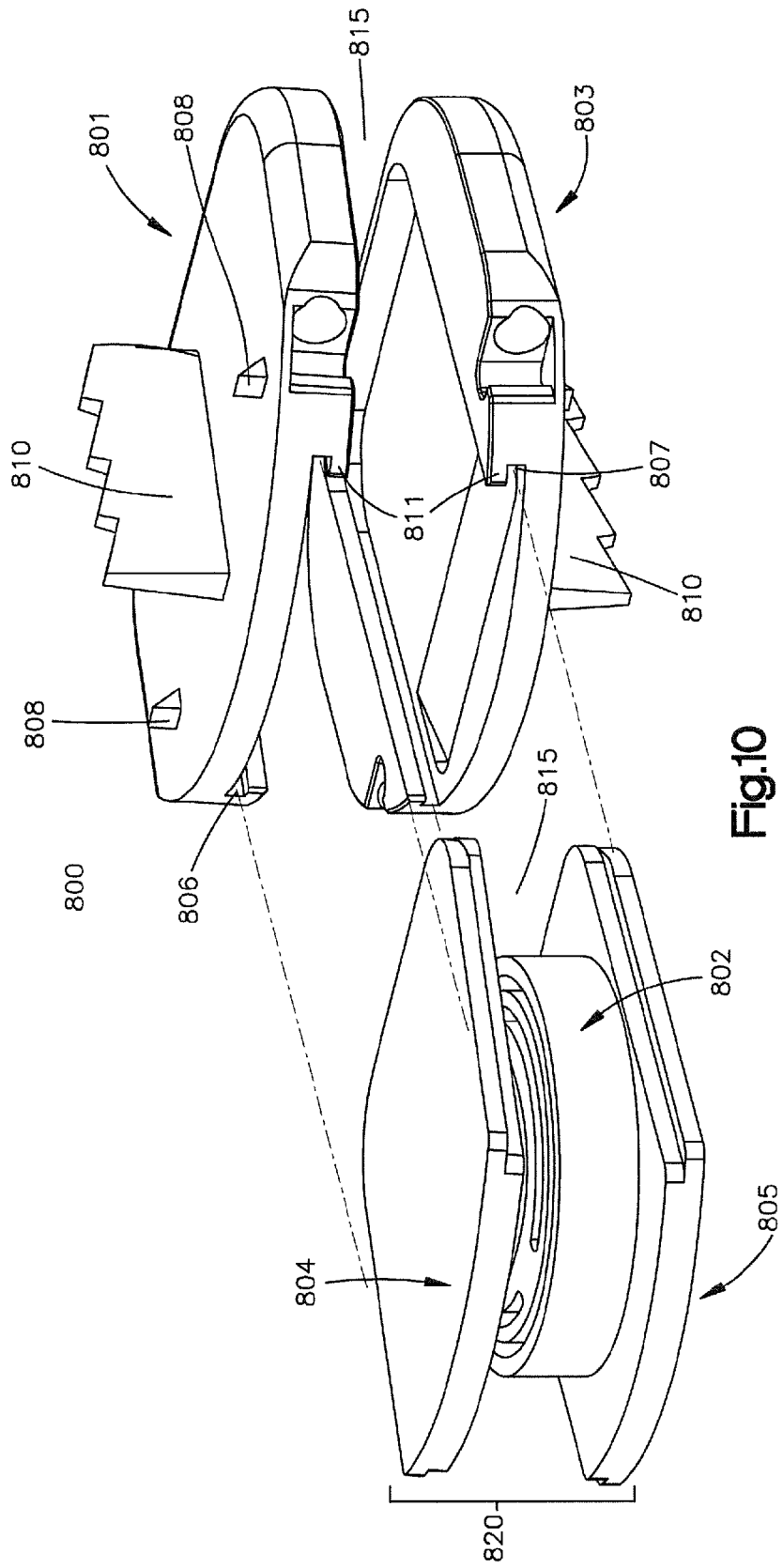
FIG. 10 is a side perspective, partially exploded view of the intervertebral spacer device of FIG. 9.

Referring to FIG. 9 and FIG. 10 in a fourth preferred embodiment, a spacer 800 includes upper and lower plates 801, 803 formed as upper and lower intermediate members 804, 805. An articulation element 802 is operatively associated with, and preferably attached to intermediate members 804, 805 to form core assembly 820. The articulation element 802 is preferably fixedly attached to the upper and lower intermediate members 804, 805 in any of the methods described above to attach the articulation element 102 to the upper and lower plates 101, 103 of the first preferred embodiment including by press-fit, welding, bonding, use of fasteners, as described and configured in FIGS. 1-6, or any other joining mechanism or means now known or later discovered, or the articulation element 802 and intermediate members 804, 805 may be fabricated monolithically out of one piece of material. The spacer 800 may further include upper and lower end plates 801, 803, and may further include additional vertebral attachment means, such as keels 810, spikes 808, ridges (see, i.e., 101c, 103c), or any other attachment means now known or later discovered. The upper and lower end plates 801, 803, in the fourth preferred embodiment, further include recessed portions 806, 807 for receiving the intermediate members 804, 805, which slide into the recessed portions 806, 807 during assembly or during the procedure. The upper and lower end plates 801, 803 may further include shoulders 811 for guiding the intermediate members 804, 805 into the recessed portions 806, 807. To avoid the intermediate members 804, 805, and the articulation element 802, from backing or sliding out of the recessed portions 806, 807 and to vertically secure the intermediate members 804, 805 to the upper and lower plates 801, 803, a fastening means such as press-fitting, welding, bonding, use of fasteners, bolts, screws, snap-lock or any joining mechanism or means now known or later discovered, may preferably be used to fix the intermediate members 804, 805 to the upper and lower end plates 801, 803. One advantage provided by the fourth embodiment is that a "kit" may be created, with various core elements 820 providing different heights, relative stiffnesses, and/or limited movements, which may fit into upper and lower endplates, depending specifically upon the patient's need. In addition, the upper and lower endplates 801, 803 may be mounted initially to vertebrae V1, V2, the vertebrae may be distracted and the intermediate members 804, 805 and the articulation element 802 may slide into the endplates 801, 802, in situ.

The motion and dampening capabilities of the spacer 800 of the fourth preferred embodiment may be restricted or completely blocked through the insertion of a rigid insert, such as an additional clip (not shown) to block and prevent relative movement between the intermediate members 804, 805 and the articulation element 802. The clip (not shown) may be placed about or around the articulation element 802 or a portion of the articulation element 802 and block or prevent the intermediate members 804, 805 from moving closer together and/or farther apart. The preferred spacer 800 may be blocked from articulation in cases where the condition of the spine degrades to a point where the vertebrae V1, V2 must be fused. The insertion of such a clip may be conducted by relatively minor surgical intervention. Alternatively, in the case where the articulation element 802 with the intermediate members 804, 805 has been used, the core assembly 820 may be removed and replaced by a rigid insert (not shown) while the upper and lower end plates 801, 803 remain attached to the vertebrae V1, V2.

To minimize the risk of bony in-growth into the intervertebral spacer 800, a protective sheet (not shown) may be wrapped around the intervertebral spacer 800. Such a protective sheet may be made out of a biocompatible elastomer or a fabric-like structure, or any other suitable material now known, or later discovered. The spacer 800 also may preferably have a silicone, polyurethane elastomer, polycarbonate urethane (PCU), or any other suitable filler, injected into the spaces and gaps 815 in the spacer 800 to provide load bearing and load sharing capabilities.

Figure 11:
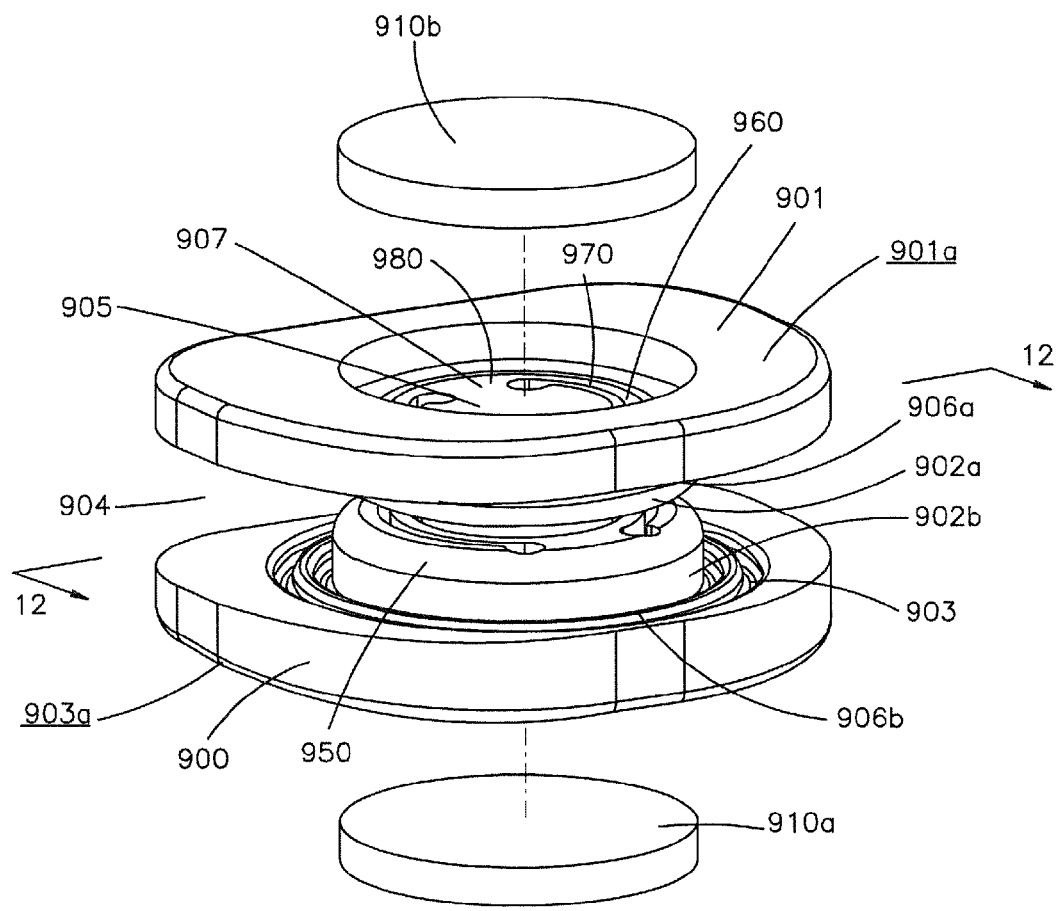
FIG. 11 is a front perspective, partially exploded view of a intervertebral spacer device of in accordance with a fifth preferred embodiment of the present invention.
Figure 12:
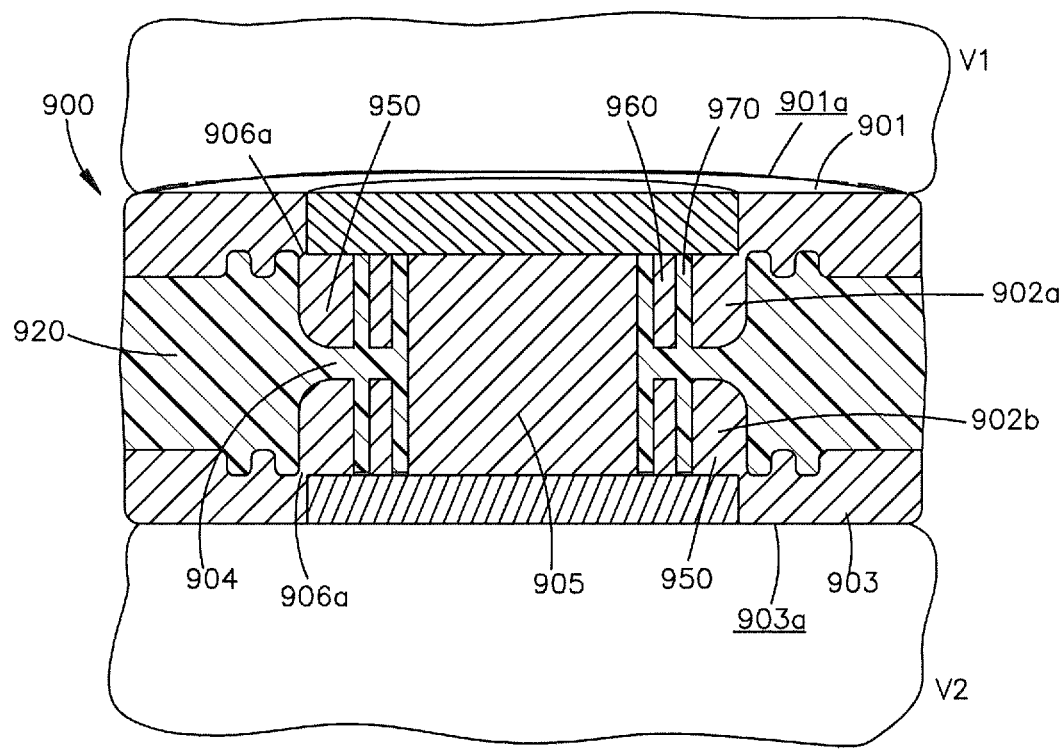
FIG. 12 is a cross-sectional view of the intervertebral spacer device of FIG. 11 taken alone line 12-12 of FIG. 11 in an assembled configuration.
Figure 13:
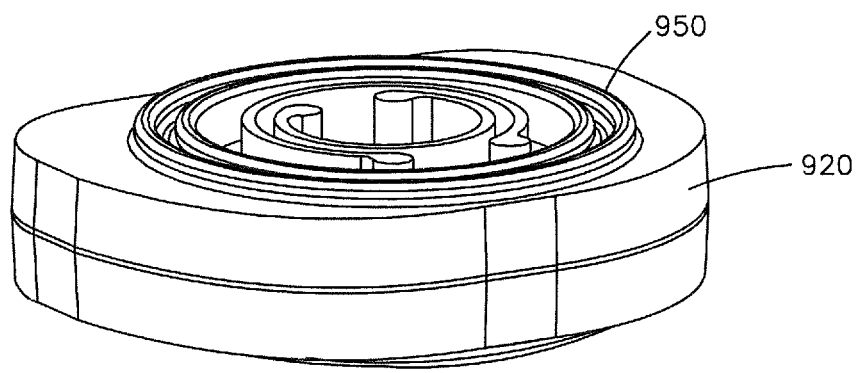
FIG. 13 is a top perspective view of a elastic element of the intervertebral spacer device of FIG. 11.

Referring to FIGS. 11-13, in a fourth preferred embodiment, a spacer 900 includes upper and lower plates 901, 903, shaft element 905, and dual articulation elements 902a, 902b. The spacer 900 may optionally further include plate inserts 910a, 910b, and an elastic element 920. The upper and lower plates 901, 903, dual articulation elements 902a, 902b, and shaft element 905 may preferably be fabricated out of one piece of material. An outermost segment 950 of each articulation element 902a, 902b may preferably be operatively associated with, or fabricated to connect to the upper and lower plates 901, 903, as shown at 906a, 906b. The connecting element 906a, 906b may be a bridging element. The shaft element 905 preferably connects the upper articulation element 902a with the lower articulation element 902b. The upper and lower plates 901, 903, may preferably include outer surfaces 901a, 903a having a recessed portion 907 for receiving plate inserts 910a, 910b. The plate inserts 910a, 910b, may preferably be operatively associated with and connected to the upper and lower plates 901, 903.

Each dual articulation element 902a, 902b, preferably includes segments 202, bridging elements 203, and spaces 201 between the segments 202. The dual articulation elements 902a, 902b, may be separated preferably by an open space 904 that provides room for the articulation elements 902a, 902b to move without contact between the dual articulation elements 902a, 902b, or contact between the upper and lower plates 901, 903. The control shaft 905 preferably vertically connects the articulation elements 902a, 902b. The spacer 900 preferably provides at least six degrees of motion, including, flexion, extension, lateral bending, axial rotation, horizontal shifting, and axial dampening generally with little or no friction, as described above.

Preferably, the spacer 900 is constructed of a biocompatible metal and preferably the upper and lower plates 901, 903, the dual articulation elements 902a, 902b, and the shaft 905 are monolithically formed from a single block of metal material. One preferred manner of forming the spacer 900 is to form recessed portions 907 in the upper and lower portions of the block. Thereafter, spaces 201 in the form of concentric "C" shaped rings may be formed in the block by machining to form the segments 202 and bridging elements 203 and the shaft 905. Thereafter the open space 904 located in the middle and around the periphery of the block may be formed by machining to result in the spacer 900. The steps of forming the spacer 900 from a single block of material may be varied, such as for example by forming the space 904 before the "C"-shaped spaces 201. Spaces 201 may be formed from one side of the block and formed so that the upper articulation element 902a is the same as the lower articulation element 902b. Alternatively, upper articulation element 902a may be formed to be different than lower articulation element 902b, and may in one embodiment be formed by creating spaces 201 from different sides of the substrate block and in different patterns.

The elastomer element 920 may be operatively associated with and preferably attached between the upper and lower plates 901, 903. The elastomer element 920, such as silicone, polyurethane elastomer, polycarbonate urethane, or any other suitable biocompatible material, is preferably injected into and around the core of the spacer 900 and/or into the space 904. The elastomer element 920 preferably fills some or all voids in between upper and lower plates 901, 903, dual articulation elements 902a, 902b, and any other desirable areas. The elastomer element 920 is preferably a load sharing component of the invertebral spacer 900, providing some absorption of flexion, extension, lateral bending, axial rotation, horizontal shifting, and axial compression forces. The elastomer element 920 may be constructed of a silicone based material, polycarbonate-urethane, or any suitable biocompatible elastomer material. The spacer 900 of the fifth preferred embodiment may preferably possess the same motion and resistance properties as elements described in the first, second, third, and fourth preferred embodiments.

As will be appreciated by those skilled in the art, any or all of the components described herein may be provided in sets or kits so that the surgeon may select various combinations of components to form an implant and create a disc replacement system which is configured specifically for the particular needs/anatomy of a patient. It should be noted that one or more of each component may be provided in a kit or set. In some kits or sets, the same component or part may be provided in different shapes and/or sizes. The surgeon or staff may mix and match the parts to create the spacer 100, 500, 700, 800, 900 before or during the procedure.

A preferred surgical technique to implant the spacers 100, 500, 700, 800, 900 or other spacers comprises the steps of: (1) exposing the intervertebral disc and the adjacent vertebral bodies of adjacent vertebrae V1, V2; (2) cleaning out the intervertebral space and removing disc tissue and cartilage fragments from between the vertebral bodies; (3) optionally distracting the intervertebral space with a spreader to restore the height of the intervertebral space; (4) optionally, inserting a trial implant to determine the final size, height, and lordosis or kyphosis angle, as well as the position of the spacer to be inserted; (5) optionally, chiseling or milling to create a keel bed, groove, or channel for the spacer, if necessary or otherwise preparing the endplates of the vertebrae to accept the spacer; (6) inserting the spacer into the prepared area between the vertebrae V1, V2; and (7) closing the incision.

Another preferred surgical technique generally comprises the steps of: (1) exposing the intervertebral disc and the adjacent vertebral bodies of the adjacent vertebrae V1, V2; (2) cleaning out the intervertebral space and removing disc tissue and cartilage fragments from between the vertebral bodies; (3) optionally distracting the intervertebral space with a spreader to restore the height of the intervertebral space; (4) optionally, inserting a trial implant to determine the final size, height, or lordosis or kyphosis angle as well as the position of the spacer to be inserted; (5) optionally, chiseling to create a keel bed, groove, or channel for the spacer, if necessary, or otherwise preparing the endplates of the vertebrae V1, V2 to accept the spacer; (6) inserting the endplates; (7) inserting the articulation element by sliding it into the recesses of the upper and lower plates; and (8) closing the incision.

The preferred spacers 100, 500, 700, 800, 900 of the present application are generally mounted between two adjacent vertebrae V1, V2 after removal of a vertebral disc, or portions of the vertebral disc as shown in FIG. 14. However, the spacers 100, 500, 700, 800, 900, are not limited to being mounted between two adjacent vertebrae V1, V2, and may be designed and configured for mounting between two vertebrae V1, V2 where an intervening vertebrae or vertebral body has been removed. Additionally, while the spacers 100, 500, 700, 800, 900 are described as generally for use in the spine, those of ordinary skill in the art will recognize that the spacers 100, 500, 700, 800, 900 may have other uses and may be used as a prosthesis for other joints, such as, for example, the shoulder, elbow, wrist, hip, knee, ankle, foot, toe and finger. The spacers may also be used for non-medical applications.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. An intervertebral spacer for placement between an upper vertebra and a lower vertebra, the intervertebral spacer comprising:
    a first endplate having an outer surface configured to contact one of the upper vertebra and lower vertebra, the first endplate having an inner surface opposite the outer surface and a pin element extending from the inner surface;
    a second endplate having an outer surface configured to contact the other of the upper vertebra and lower vertebra, the second endplate having an inner surface opposite the outer surface of the second endplate and a recessed portion extending into the inner surface of the second endplate, the inner surface of the first endplate facing the inner surface of the second endplate in an assembled configuration; and
    at least one articulation element having an outer perimeter, a plurality of segments disposed within the outer perimeter, a space separating adjacent ones of the plurality of segments and a bridging element connecting adjacent ones of the plurality of segments, the bridging element including a first sidewall and a second sidewall spaced from the first sidewall in a circumferential direction, the space including a first terminal end defined by the first sidewall, a second terminal end defined by the second sidewall, and a length that extends continuously from the first terminal end in the circumferential direction to the second terminal end, the at least one articulation element having an outermost one of the plurality of segments and an innermost one of the plurality of segments that is disposed within the outermost segment, such that the outermost segment is positioned closer to the outer perimeter than the innermost segment,
    wherein in the assembled configuration, the at least one articulation element receives the pin element, and the at least one articulation element is received within the recessed portion to permit relative movement of the endplates by flexing of the at least one articulation element without opposed surfaces of adjacent segments rubbing against each other.

2. The spacer of claim 1, wherein the segments are concentric O-shaped rings.

3. The spacer of claim 1, wherein when the first and second endplates move relative to each other, the segments elastically deflect relative to each other such that respective spaces between the segments change shape.

4. The spacer of claim 1, wherein when the endplates move relative to each other, the bridging elements elastically deflect.

5. The spacer of claim 1, wherein the at least one articulation element further comprises at least one intermediate one of the plurality of segments interposed between the innermost segment and the outermost segment.

6. The spacer of claim 1, wherein one of the bridging elements connects the at least one articulation element to one of the first and second endplates.

7. The spacer of claim 1, wherein the outermost segment is fixedly connected to one of the first and second endplates and the innermost segment is fixedly connected to the other one of the first and second endplates.

8. The spacer device of claim 1, wherein the spacer has a vertical axis, and a height of each adjacent segment along the vertical axis increases from the outermost segment towards the innermost segment.

9. The spacer of claim 1, wherein the spacer has a vertical axis, and a height of each adjacent segment along the vertical axis decreases from the outermost segment towards the innermost segment.

10. The spacer of claim 1, wherein the spacer has a vertical axis, and the positioning of ends of adjacent segments alternates up and down along the vertical axis, forming a zig-zag configuration.

11. The spacer of claim 1, wherein the outermost segment is received within the recessed portion in the assembled configuration.

12. The spacer of claim 11, wherein an inner wall defines the recessed portion, the inner wall angled in an outwardly direction toward a perimeter of the endplate in which the inner wall is formed.

13. The spacer of claim 1, further comprising a gapped area between the at least one articulation element and one of the endplates to permit the segments to move into this gapped area.

14. The spacer of claim 1, wherein the inner most segment includes an inner wall that defines an inner space and the pin element is received within the inner space in the assembled configuration.

15. The spacer device of claim 14, wherein the pin element is fixedly connected to the first endplate, extends toward the inner surface of the second endplate in the assembled configuration, and is press fit into at least one of the spaces separating segments of the at least one articulation element.

16. The spacer of claim 1, wherein the first endplate, the second endplate, and at least one articulation element comprise a single, monolithic body of material.

17. The spacer of claim 1, further comprising a second articulation element having a plurality of segments each separated by at least one space, and at least one bridging element connecting the adjacent segments.

18. The spacer device of claim 1, further comprising an elastomer element filling gaps and spaces between the first and second endplates.

19. The spacer of claim 1, wherein the space separates the adjacent ones of the plurality of segments along an entirety of the circumferential length, such that the adjacent ones of the plurality of segments are joined only by the bridging element.

20. An intervertebral spacer for placement between an upper vertebra and a lower vertebra, the intervertebral spacer comprising:
a first endplate having an outer surface configured to contact one of the upper vertebra and lower vertebra, the first endplate having an inner surface opposite the outer surface;
a second endplate having an outer surface configured to contact the other of the upper vertebra and lower vertebra, the second endplate having an inner surface opposite the outer surface of the second endplate, the inner surface of the first endplate facing the inner surface of the second endplate in an assembled configuration; and
at least one articulation element having a central axis, an outer perimeter extending circumferentially about the central axis and spaced from the central axis along a radial direction, and a plurality of segments, each of the plurality of segments separated from an adjacent one of the plurality of segments in the radial direction by a space, each of the plurality of segments connected to the adjacent one of the plurality of segments by one of a plurality of bridging elements, such that each one of the plurality of bridging elements is spaced from the central axis a distance along the radial direction that is different than the distance of all the others of the plurality of bridging elements, the at least one articulation element having an outermost one of the segments and an innermost one of the plurality of segments that is disposed within the outermost segment, such that the outermost segment is positioned closer to the outer perimeter than the innermost segment;
wherein in the assembled configuration the innermost segment contacts the first endplate, the outermost segment contacts the second endplate, the innermost segment does not contact the second endplate, and the outermost segment does not contact the first endplate, such that the first and second endplates are moveable relative to one another by flexing of the at least one articulation element.

21. The spacer of claim 20, wherein when the first and second endplates move relative to each other, the segments elastically deflect relative to each other such that the respective space between adjacent segments changes shape.

22. The spacer of claim 21, wherein when the endplates move relative to each other, the bridging elements elastically deflect and opposed surfaces of adjacent segments do not contact each other.

23. The spacer of claim 20, wherein the at least one articulation element further comprises at least one intermediate one of the plurality of segments interposed between the innermost segment and the outermost segment.

24. The spacer of claim 23, wherein when the spacer is in the assembled configuration, the intermediate one of the plurality of segments does not contact either of the first and second endplates.

25. The spacer of claim 20, wherein the innermost segment includes an inner wall that defines an inner space and the first endplate further includes a pin element that is received within the inner space when the spacer is in the assembled configuration.

26. The spacer of claim 25, wherein the second endplate includes a recessed portion that extends into the inner surface of the second endplate, such that in the assembled configuration the outer perimeter of the articulation element is at least partially received within the recessed portion.

27. The spacer of claim 20, wherein the second endplate includes a recessed portion that extends into the inner surface of the second endplate, such that in the assembled configuration the outer perimeter of the articulation element is at least partially received within the recessed portion.

28. The spacer of claim 20, wherein the articulation element defines an upper surface that faces the inner surface of the first endplate in the assembled configuration, an outer surface that faces the inner surface of the second endplate in the assembled configuration, each of the spaces separating adjacent ones of the plurality of segments extends from the upper surface through the lower surface.

29. An intervertebral spacer for placement between an upper vertebra and a lower vertebra, the intervertebral spacer comprising:
a first endplate having an outer surface configured to contact one of the upper vertebra and lower vertebra, the first endplate having an inner surface opposite the outer surface;
a second endplate having an outer surface configured to contact the other of the upper vertebra and lower vertebra, the second endplate having an inner surface opposite the outer surface of the second endplate, the inner surface of the first endplate facing the inner surface of the second endplate in an assembled configuration; and
at least one articulation element having an upper surface that faces the inner surface of the first endplate in the assembled configuration, a lower surface that faces the inner surface of the second endplate in the assembled configuration, and an outer perimeter that extends from the upper surface to the lower surface, the articulation element having a plurality of segments disposed within the outer perimeter, each of the plurality of segments being separated from an adjacent one of the plurality of segments by one of a plurality of spaces, and each of the plurality of segments being connected to the adjacent one of the plurality of segments by one of a plurality of bridging elements, wherein at least a portion of each of the plurality of spaces individually defines a height that extends from the upper surface through the lower surface of the articulation element.

30. The spacer of claim 29, wherein the one of the plurality of bridging elements includes a first sidewall and a second sidewall spaced from the first sidewall in a circumferential direction, and the one of the plurality of spaces includes a first terminal end defined by the first sidewall, a second terminal end defined by the second sidewall, and a length that extends continuously from the first terminal end in the circumferential direction to the second terminal end.

31. The spacer of claim 29, wherein the articulation element includes a central axis extending between the upper and lower surfaces, a radial direction measured from the central axis toward the outer perimeter, and each the plurality of bridging elements is spaced from the central axis a distance measured in the radial direction, the distance of each of the plurality of bridging elements being different than the distance of all others of the plurality of bridging elements from the central axis along the radial direction.

* * * * *